(12) United States Patent
Jacobson et al.

(10) Patent No.: US 9,155,299 B2
(45) Date of Patent: Oct. 13, 2015

(54) BONDED FIBER MATRIX CONTAINING ENCAPSULATION COMPLEX

(75) Inventors: Richard Martin Jacobson, Chalfont, PA (US); Bennett Clayton Ward, Midlothian, VA (US); Jian Xiang, Midlothian, VA (US)

(73) Assignee: AGROFRESH INC., Collegeville, PA (US)

( * ) Notice: Subject to any disclaimer, the term of this patent is extended or adjusted under 35 U.S.C. 154(b) by 470 days.

(21) Appl. No.: 13/510,069

(22) PCT Filed: Nov. 17, 2010

(86) PCT No.: PCT/US2010/056961
§ 371 (c)(1),
(2), (4) Date: May 16, 2012

(87) PCT Pub. No.: WO2011/062950
PCT Pub. Date: May 26, 2011

(65) Prior Publication Data
US 2012/0272572 A1    Nov. 1, 2012

Related U.S. Application Data

(60) Provisional application No. 61/281,554, filed on Nov. 18, 2009.

(51) Int. Cl.
*A01N 25/34* (2006.01)
*A01N 25/28* (2006.01)
*A01N 27/00* (2006.01)

(52) U.S. Cl.
CPC ............... *A01N 25/34* (2013.01); *A01N 25/28* (2013.01); *A01N 27/00* (2013.01)

(58) Field of Classification Search
None
See application file for complete search history.

(56) References Cited

U.S. PATENT DOCUMENTS

| | | | |
|---|---|---|---|
| 6,770,600 B1 * | 8/2004 | Lamola et al. | 504/357 |
| 2005/0260907 A1 | 11/2005 | Chang et al. | |
| 2010/0144533 A1 | 6/2010 | Baier et al. | |
| 2011/0143004 A1 | 6/2011 | Wood et al. | |

FOREIGN PATENT DOCUMENTS

EP    1203525    5/2002

* cited by examiner

*Primary Examiner* — Carlos Azpuru
*Assistant Examiner* — Casey Hagopian
(74) *Attorney, Agent, or Firm* — Ladas & Parry LLP

(57) ABSTRACT

Provided are a device comprising
(a) a three-dimensional structure comprising a plurality of fibers, and
(b) powder particles contained in and/or affixed to said structure, wherein said powder particles comprise one or more volatile compound in an encapsulation complex with a molecular encapsulation agent, a method for releasing a volatile compound from a molecular encapsulation complex using such a device, and an apparatus or system for performing such a method.

11 Claims, No Drawings

BONDED FIBER MATRIX CONTAINING ENCAPSULATION COMPLEX

BACKGROUND

Handling volatile compounds presents a variety of problems. One method of making a volatile compound easier to handle is to form a molecular encapsulation complex in which a molecular encapsulating agent encapsulates the molecules of the volatile compound. When it is desired to make use of the volatile compound, one common method involves bringing the molecular encapsulation complex into contact with a release compound, a compound that, when it contacts an encapsulation complex, promotes or causes release of the volatile compound from the molecular encapsulation complex.

In some cases, the molecular encapsulation complex is in the form of a powder, which may optionally be blended with other solid particles of other materials to form a blended powder. Such powders are generally easier to store, to transport, and/or to use than the pure volatile compound.

However, such powders do not solve all the problems associated with the use of the volatile compounds. For example, when using a release compound to release the volatile compound from such a powder, the contact between the powder and the release compound is not intimate, and it is necessary to take some measure to enhance the release of the volatile compound. Such measures include, for example, waiting an undesirably long time for the volatile compound to release, or providing some mechanical aid (e.g., shaking, stirring, effervescent action, etc.). U.S. Pat. No. 6,426,319 describes a composition containing a molecular encapsulation complex of a molecular encapsulating agent with a cyclopropene compound, mixed with a water absorbent material.

It is desired to provide a device that improves intimate contact between replacement compound and molecular encapsulation complex.

Additionally, powders present difficulties in handling because they flow and make dust. Therefore it is also desired to provide a device that contains molecular encapsulation agent and that has a fixed structure.

SUMMARY OF CERTAIN EMBODIMENTS OF THE INVENTION

In a first aspect of the present invention, there is provided a device comprising
(a) a three-dimensional structure comprising a plurality of fibers, and
(b) powder particles contained in and/or affixed to said structure, wherein said powder particles comprise one or more volatile compound forms an encapsulation complex with a molecular encapsulation agent.

In a second aspect of the present invention, there is provided a method of releasing a volatile compound. The method comprising providing a release device comprising
(a) a three-dimensional structure comprising a plurality of fibers, and
(b) powder particles contained in or affixed to said structure, wherein said powder particles comprise one or more volatile compound in an encapsulation complex with a molecular encapsulation agent.
The method further comprises bringing the predetermined release complex into contact with the molecular encapsulation complex so that the molecular encapsulation complex releases the volatile compound.

In a third aspect of the present invention, there is provided an apparatus or system for delivering a volatile compound to a target. The apparatus or system comprises a container defining an interior space configured for receiving the target and at least one release device comprising
(a) a three-dimensional structure comprising a plurality of fibers, and
(b) powder particles contained in and/or affixed to said structure, wherein said powder particles comprise one or more volatile compound in an encapsulation complex with a molecular encapsulation agent selected and configured to release the volatile compound when said encapsulation complex comes into contact with a predetermined release compound,
the at least one release device being disposed so that it is in fluid communication with an atmosphere of the interior space.

DETAILED DESCRIPTION

As used herein, "ambient temperature range" means the range of temperatures from $-40°$ C. to $40°$ C.

As used herein, when a ratio is recited to be "X:1 or higher," it is meant that the ratio is Y:1, where Y is equal to or greater than X. Similarly, when a ratio is recited to be "R:1 or lower," it is meant that the ratio is S:1, where S is equal to or less than R.

As used herein, a "fiber" is a material that is solid over the ambient temperature range, that has one dimension much larger than the other two dimensions, that has a cross-section (in the direction perpendicular to the long dimension) that is typically (but not necessarily) a substantially uniform shape, and that has cross-sectional area of $4 \text{ mm}^2$ or less. A fiber has aspect ratio (as measured by the length divided by the square root of the cross-sectional area) of 10:1 or higher.

As used herein, a "fiber structure" is a collection of fibers that combine to form a porous body. The collection of fibers may be woven or may be non-woven, in which case the structural integrity of the porous body is maintained through bonding of the fibers to one another and/or through a containment structure such as a sheath. Bonded fiber structures are formed from webs of thermoplastic fibrous material comprising an interconnecting network of highly dispersed fibers bonded to one another at spaced apart points of contact. Depending on the nature of the fibers and the bonds between them, these structures may be substantially self-sustaining, three-dimensional porous bodies that provide tortuous fluid flow paths, high fiber surface areas and porosity, and may be formed in a variety of sizes and shapes.

As used herein, a "multicomponent fiber" is a fiber in which two or more different chemical substances (the "components") are placed in discrete portions of the fiber body. If exactly two components are present, the fiber is herein called a "bicomponent fiber." A fiber made from a single chemical substance is known herein as a "monocomponent fiber."

A "polymer," as used herein and as defined by F W Billmeyer, Jr. in *Textbook of Polymer Science,* 2nd edition, 1971, is a relatively large molecule made up of the reaction products of smaller chemical repeat units. Polymers may have structures that are linear, branched, star shaped, looped, hyperbranched, crosslinked, or a combination thereof; polymers may have a single type of repeat unit ("homopolymers") or they may have more than one type of repeat unit ("copolymers"). Copolymers may have the various types of repeat units arranged randomly, in sequence, in blocks, in other arrangements, or in any mixture or combination thereof.

Polymer molecular weights can be measured by standard methods such as, for example, size exclusion chromatography (SEC, also called gel permeation chromatography or GPC). Generally, polymers have weight-average molecular weight (Mw) of 1,000 or more. Polymers may have extremely high Mw; some polymers have Mw above 1,000,000; typical polymers have Mw of 1,000,000 or less. Some polymers are crosslinked, and crosslinked polymers are considered to have infinite Mw. Some polymers are characterized by Mn, the number-average molecular weight.

Molecules that can react with each other to form the repeat units of a polymer are known herein as "monomers."

Two methods of characterizing polymers are the glass transition temperature (Tg) and the melt temperature (Tm). Both are measured by Differential Scanning calorimetry.

As used herein, the "softening point" is the temperature at which a polymer becomes soft enough to deform readily under mild pressure such as gravity or the pressure exerted by the dies used for making bonded non-woven webs (as described herein below). If a polymer has a melting point, then the melting point is its softening point. If a thermoplastic polymer does not have a melting point, the softening point of that polymer is a temperature above the polymer's Tg at which it deforms readily under mild pressure. For a typical thermoplastic polymer, the difference between Tg and the softening point may depend on the polymer's Mw. A polymer that is fully crosslinked will not flow, even if its Tg is below room temperature; therefore all fully crosslinked polymers are considered to have softening point higher than any temperature used for processing polymers.

A polymer that is at a temperature below its softening point is referred to herein as a "solid" polymer.

As used herein, a "fluid" is a gas or a liquid.

As used herein, a "hydrophilic" surface is a surface that attracts water. That is, a drop of water on a hydrophilic surface will wet out, have a small contact angle, and will spread relatively readily. A hydrophilic compound is a compound which, when present on a surface, will normally make that surface more hydrophilic. A hydrophobic surface is a surface that repels water, does not wet out, and has a large contact angle, and a hydrophobic compound, when present on a surface, will normally make that surface more hydrophobic.

The present invention involves the use of one or more cyclopropene compound. As used herein a cyclopropene compound is any compound with the formula

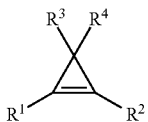

where each $R^1$, $R^2$, $R^3$ and $R^4$ is independently selected from the group consisting of H and a chemical group of the formula:

where n is an integer from 0 to 12. Each L is a bivalent radical. Suitable L groups include, for example, radicals containing one or more atoms selected from H, B, C, N, O, P, S, Si, or mixtures thereof. The atoms within an L group may be connected to each other by single bonds, double bonds, triple bonds, or mixtures thereof. Each L group may be linear, branched, cyclic, or a combination thereof. In any one R group (i.e., any one of $R^1$, $R^2$, $R^3$ and $R^4$) the total number of heteroatoms (i.e., atoms that are neither H nor C) is from 0 to 6.

Independently, in any one R group the total number of non-hydrogen atoms is 50 or less.

Each Z is a monovalent radical. Each Z is independently selected from the group consisting of hydrogen, halo, cyano, nitro, nitroso, azido, chlorate, bromate, iodate, isocyanato, isocyanido, isothiocyanato, pentafluorothio, and a chemical group G, wherein G is a 3 to 14 membered ring system.

The $R^1$, $R^2$, $R^3$ and $R^4$ groups are independently selected from the suitable groups. The $R^1$, $R^2$, $R^3$ and $R^4$ groups may be the same as each other, or any number of them may be different from the others. Groups that are suitable for use as one or more of $R^1$, $R^2$, $R^3$ and $R^4$ may be connected directly to the cyclopropene ring or may be connected to the cyclopropene ring through an intervening group such as, for example, a heteroatom-containing group.

As used herein, a chemical group of interest is said to be "substituted" if one or more hydrogen atoms of the chemical group of interest is replaced by a substituent. Suitable substituents include, for example, alkyl, alkenyl, acetylamino, alkoxy, alkoxyalkoxy, alkoxycarbonyl, alkoxyimino, carboxy, halo, haloalkoxy, hydroxy, alkylsulfonyl, alkylthio, trialkylsilyl, dialkylamino, and combinations thereof.

Among the suitable $R^1$, $R^2$, $R^3$ and $R^4$ groups are, for example, substituted and unsubstituted versions of any one of the following groups: aliphatic, aliphatic-oxy, alkylcarbonyl, alkylphosphonato, alkylphosphato, alkylamino, alkylsulfonyl, alkylcarboxyl, alkylaminosulfonyl, cycloalkylsulfonyl, cycloalkylamino, heterocyclyl (i.e., aromatic or non-aromatic cyclic groups with at least one heteroatom in the ring), aryl, hydrogen, fluoro, chloro, bromo, iodo, cyano, nitro, nitroso, azido, chlorato, bromato, iodato, isocyanato, isocyanido, isothiocyanato, pentafluorothio; acetoxy, carboethoxy, cyanato, nitrato, nitrito, perchlorato, allenyl; butylmercapto, diethylphosphonato, dimethylphenylsilyl, isoquinolyl, mercapto, naphthyl, phenoxy, phenyl, piperidino, pyridyl, quinolyl, triethylsilyl, and trimethylsilyl.

Among the suitable $R^1$, $R^2$, $R^3$ and $R^4$ groups are those that contain one or more ionizable substituent groups. Such ionizable groups may be in non-ionized form or in salt form.

Also contemplated are embodiments in which $R^3$ and $R^4$ are combined into a single group, which is attached to the number 3 carbon atom of the cyclopropene ring by a double bond. Some of such compounds are described in US Patent Publication 2005/0288189.

In some embodiments, one or more cyclopropenes are used in which one or more of $R^1$, $R^2$, $R^3$ and $R^4$ is hydrogen. In some embodiments, each of $R^1$, $R^2$, $R^3$ and $R^4$ is hydrogen or methyl. In some embodiments, $R^1$ is (C1-C4)alkyl and each of $R^2$, $R^3$, and $R^4$ is hydrogen. In some embodiments, $R^1$ is methyl and each of $R^2$, $R^3$, and $R^4$ is hydrogen, and the cyclopropene compound is known herein as "1-MCP."

In some embodiments, a cyclopropene compound is used that has boiling point at one atmosphere pressure of 50° C. or lower; or 25° C. or lower; or 15° C. or lower. Independently, in some embodiments, a cyclopropene compound is used that has boiling point at one atmosphere pressure of −100° C. or higher; −50° C. or higher; or 25° C. or higher; or 0° C. or higher.

The practice of the present invention involves one or more molecular encapsulating agent. Suitable molecular encapsulating agents include, for example, organic and inorganic molecular encapsulating agents. Suitable organic molecular encapsulating agents include, for example, substituted cyclodextrins, unsubstituted cyclodextrins, and crown ethers. Suitable inorganic molecular encapsulating agents include, for example, zeolites. Mixtures of suitable molecular encapsulating agents are also suitable. In some embodiments of the invention, the encapsulating agent is alpha cyclodextrin, beta cyclodextrin, gamma cyclodextrin, or a mixture thereof. In some embodiments of the invention, particularly when the volatile compound is 1-methylcyclopropene, the encapsulating agent is alpha cyclodextrin. The preferred encapsulating agent will vary depending upon the structure of the volatile compound or compounds being used. Any cyclodextrin or mixture of cyclodextrins, cyclodextrin polymers, modified cyclodextrins, or mixtures thereof can also be utilized pursuant to the present invention.

At least one molecular encapsulating agent encapsulates one or more volatile compounds. A volatile compound molecule encapsulated in a molecule of a molecular encapsulating agent is known herein as an "encapsulation complex." The encapsulation complexes can be prepared by any means. In one method of preparation, for example, such complexes are prepared by contacting the volatile compound with a solution or slurry of the molecular encapsulation agent and then isolating the complex.

The amount of molecular encapsulating agent can usefully be characterized by the ratio of moles of molecular encapsulating agent to moles of volatile compound. In some embodiments, the ratio of moles of molecular encapsulating agent to moles of volatile compound is 0.3:1 or higher; or 0.9:1 or higher; or 0.92:1 or higher; or 0.95:1 or higher. Independently, in some of such embodiments, the ratio of moles of molecular encapsulating agent to moles of volatile compound is 2:1 or lower; or 1.5:1 or lower. In some embodiments, the ratio of moles of molecular encapsulating agent to moles of volatile compound is 0.95:1 to 1.5:1.

In some embodiments, one or more molecular encapsulating agents encapsulate one or more cyclopropene compound.

In some embodiments, the encapsulation complex is in the form of a powder. The powder may be blended with other materials to form a blended powder. Suitable other materials include, for example, water-absorbing materials, humectants, molecular sieves, sugars, cyclodextrins, minerals, and mixtures thereof. In some embodiments, one or more sugars, such as, for example, dextrose, are used. In some embodiments, one or more minerals, such as, for example, alkali carbonates, alkali bicarbonates, alkaline earth carbonates, alkaline earth bicarbonates, and mixtures thereof are used. In some embodiments, powder containing an encapsulation complex contains dextrose, sodium bicarbonate, or a mixture thereof. In some embodiments, a water-absorbing material is used. It is contemplated that, among embodiments in which a water-absorbing material is used, a wide variety of water-absorbing materials are suitable. For example, one class of materials suitable as water-absorbing materials is ethylene glycol polymers ("PEGs"). It is contemplated that a wide variety of PEGs, including, for example, PEGs of various molecular weights, are suitable.

In some embodiments, the powder that is used in making the three-dimensional structure has ratio of weight of other particulate materials to weight of encapsulation complex of 2:1 or higher, 5:1 or higher, or 8:1 or higher. In some embodiments, the powder that is used in making the three-dimensional structure has ratio of weight of other particulate materials to weight of encapsulation complex of 50:1 or lower, or 20:1 or lower.

Some embodiments of the present invention involve the use of a release compound. The choice of release compound will depend on the nature of the molecular encapsulating agent and the nature of the volatile compound. In some embodiments, release compounds cause release of volatile compounds by forming a molecular encapsulation complex with the molecular encapsulating agent, thus displacing the volatile compound and releasing it to the atmosphere.

While the present invention is not limited to any particular theory, the mechanism by which release compounds operate are contemplated. In some cases, it is thought that a release compound may form a molecular encapsulation complex with the molecular encapsulating agent that is more stable than the molecular encapsulation complex formed by the volatile compound and the molecular encapsulating agent. In other cases, it is thought that the molecular encapsulation complex formed by the release compound may not be more stable than the molecular encapsulation complex formed by the volatile compound, but the release compound may be less volatile than the volatile compound, so that if there occurs any displacement of volatile compound by release agent, the displaced volatile compound is likely to diffuse into the atmosphere, and so, over time, most or all of the volatile compound will be released from molecular encapsulation complex.

It is contemplated that such displacement may occur because under almost all conditions, including equilibrium conditions, at which molecular encapsulation complexes exist, the volatile compounds and the release compounds (if they are present) constantly diffuse in and out of molecular encapsulation complexes with molecular encapsulating agents.

For some encapsulation complexes involving a cyclodextrin, some effective release compounds are, for example, water, surfactants, alcohols, and mixtures thereof. Suitable surfactants include, for example, anionic surfactants, nonionic surfactants, cationic surfactants, and mixtures thereof. Suitable alcohols include, for example, alkyl alcohols with 1 to 10 carbon atoms. In some embodiments, water is used as a release compound, either in liquid form or gaseous form or a mixture thereof. In some embodiments, gaseous water is used as a release compound. The choice of release agent is normally dependent on the specific molecular encapsulation complex being used.

In some embodiments, a release compound may be used as part of a mixture with other compounds. For example, in those embodiments in which liquid water is used as a release compound, the water may be present as pure water or as any aqueous composition. For another example, in those embodiments in which gaseous water is used as a release compound, the water may be present in a mixture with other gases. Such other gases may be, for example, any or all of the gases normally found in air, or may be, for another example, any or all of the gases used in controlled-atmosphere storage of plants or plant parts.

The practice of the present invention involves the use of one or more fibers that may be used to form fiber structures that may be used as carriers for the encapsulated agents described. These fibers are typically multicomponent fibers, but monocomponent fibers may be used. The components in a multicomponent fiber may be arranged in any configuration. Fibers may have any cross-sectional shape, including, for example, circular, elliptical, oval, rectangular, or more complex shapes (including, for example, multi-lobal and crenulated shapes and shapes with one or more flat side, one or more corner, one or more convex side, one or more concave side, or a combination thereof).

In some embodiments, one or more of the components of a fiber is a polymer. In some embodiments, a fiber is used in which each component is a polymer, and that fiber is known herein as a "polymeric fiber."

Polymers suitable for use as a component in a polymeric fiber include any polymer that is solid over the ambient temperature range. Some suitable polymers are, for example, hydrocarbon resins, polyesters, polyamides, fluoropolymers, vinyl polymers other than hydrocarbon resins, polyethers, and blends thereof.

Suitable hydrocarbon resins include, for example, polyethylene, polypropylene, polymers of diene resins, and copolymers thereof. Suitable polyesters include, for example, polyalkylene terephthalate polymers and copolymers (in which the alkylene group may be, for example, ethylene or butylene), and polycarbonates. Suitable polyamides include, for example, nylon 6, nylon 66, and copolymers thereof. Suitable polyethers include, for example, acetal homopolymers and copolymers, and polyalkylene glycol (in which the alkylene group may be, for example, ethylene or propylene).

Suitable vinyl polymers other than hydrocarbon resins include, for example, acrylate polymers, homopolymers and copolymers of styrene, polymers and copolymers of vinyl alcohol (including, for example, copolymers of ethylene and vinyl alcohol), copolymers of diene monomers, polymers and copolymers of vinyl chloride, and homopolymers and copolymers of vinyl acetate. Some suitable acrylic polymers include, for example, polymers and copolymers of (meth) acrylic acid, esters of (meth)acrylic acid, amides of (meth) acrylic acid, acrylonitrile, copolymers of one or more acrylic monomer with one or more monomer selected from styrene, substituted styrenes, ethylene, vinyl acetate, other non-acrylic monomers, and mixtures thereof.

In some embodiments, the fibers include one or more bicomponent fiber. Some suitable configurations of the components in bicomponent fibers include, for example, side-by-side configuration and core-sheath configuration. Side-by-side fibers have a uniform cross section in which each component forms a single continuous region that is in contact with the other component and with the external boundary of the fiber. Core-sheath fibers have a uniform cross section in which one component surrounds the other.

Multicomponent fibers that have more than two components may have the components, for example, in a side-by-side configuration, a core-sheath configuration, or a combination thereof. Multicomponent fibers may also have an "islands-in-the-sea" configuration in which multiple fiber components ("islands") are disposed within a matrix component ("sea") that defines the outer surface of the fiber.

The various components may be chosen for a variety of reasons. For example, one polymer may be more expensive than another; the inexpensive polymer may be chosen to provide most of the mass of the fiber, while a small amount of the expensive polymer may be included because it brings some desirable property to the fiber. For another example, a strong polymer with a relatively high softening point may be chosen for the core of a core-sheath fiber, while a polymer with a relatively low softening point may be chosen for the sheath of that fiber to enhance the fibers bonding characteristics.

In some embodiments involving core-sheath polymeric bicomponent fibers, one or more of the following combinations of core polymer and sheath polymer is used: core of polypropylene and sheath selected from polyethylene and copolymers of ethylene with one or more alkene monomer having 3 to 8 carbons; core of polyethylene terephthalate, polybutylene terephthalate, or other polyester and sheath of polyethylene or copolymers of ethylene with other monomers; core of polypropylene or of polybutylene terephthalate and sheath of polyethylene terephthalate or copolymers thereof; core of polyethylene terephthalate, polybutylene terephthalate, or other polyester and sheath of copolymers of polyethylene terephthalate or other copolyesters.

Some suitable multicomponent fibers (herein called "soft surface" fibers), are multicomponent polymeric fibers in which the component with the lowest softening point of all the components in that fiber is present in a configuration in which that component defines all or part of the external boundary of the fiber. For example, the component with the lowest softening point could be one component of a side-by-side bicomponent fiber. For another example, the component with the lowest softening point could be the outermost component in a core-sheath bicomponent fiber.

In soft-surface fibers, it is useful to note the difference in softening point between the lowest softening point among the components and the highest softening point among the components. In some embodiments, that difference is 10° C., or 20° C., or 50° C., or 100° C.

In the practice of the present inventions, fibers may be formed and brought together by any method to form the three-dimensional structure. It is contemplated that the three-dimensional structure may be a woven or non-woven web of fibers. In particular embodiments, the three dimensional structure is a non-woven web of highly dispersed fibers bonded to each other at points of contact.

The fibers in the three-dimensional structure, after it is formed, are in some arrangement in space other than all lying in the same flat plane. The fibers are dispersed in such a way that they form a structure that occupies space and is therefore three-dimensional. In some embodiments, the three-dimensional fiber structure is relatively thick (i.e., having a smallest dimension of 3 mm or more). In other embodiments, the three-dimensional structure may be relatively thin (i.e., having a smallest dimension of less than 3 mm); such structures may be, for example, fabrics, which may be woven or non-woven.

The fibers used in the present invention may be or may not be multicomponent fibers. Independent of the composition, the fibers in suitable fabrics may or may not be bonded to each other at points of contact. Embodiments in which fibers are not bonded to each other at points of contact are known herein as "unbonded" embodiments. If the fibers are not bonded to each other at points of contact, it is contemplated that they are part of a woven fabric or are otherwise constrained in a spatial relationship to other fibers (e.g., by a polymeric sheath) and therefore are considered herein to be part of a fiber structure.

Except in unbonded embodiments, in most or all locations throughout the three-dimensional structure after it is formed, the fibers are bonded to each other at points of contact between fibers, and there are expanses of surface area of fiber that are not in contact with other fibers and that do not participate in a bond with another fiber. For such a structure the bonds are known herein as "spaced apart" bonds.

It is contemplated that the three-dimensional structure, after it is formed, will be porous; that is, it will have significant void volume within the structure in between the fiber surfaces. It is contemplated that this structure provides a high surface area of fiber. It is also contemplated that the fiber-free volumes will connect with each other to form pathways through which a fluid could move. In some embodiments, such a pathway will be tortuous.

In some embodiments, soft-surface fibers are initially brought into contact to form a web in which the fibers are not bonded or are only loosely bonded. The web is then exposed to an elevated temperature that is above the softening point of a bondable fiber component that defines at least a portion of the outer surface of the fiber. In some embodiments, the elevated temperature may be established so as to be below the softening point of one or more other components of the fiber. The web is optionally exposed to pressure at the same time it is exposed to elevated temperature. It is contemplated that, at the elevated temperature, some or all of the bondable fiber component will deform at points of contact with itself and/or other fibers and will form fiber bonds at such points of contact when the bondable fiber component cools below its softening point.

The fibers used for making the three-dimensional structure may be staple or filament fibers or a mixture thereof. The fibers may be formed by any known technique including but not limited to melt spinning, spunbonding, dry spinning, wet spinning, and melt blowing. Fibers produced by these processes may be immediately formed into a bonded or unbonded web or may be carded/through air bonded, carded/needlepunched.

In one suitable method of forming and gathering fibers, a plurality of polymeric soft-surface multicomponent fibers are melt-blown to form a network of highly dispersed and randomly spaced fibers. Hot air is used to draw and attenuate the fibers upon extrusion from a melt-blow spin beam; the fibers are then collected and cooled to form a randomly distributed loosely bonded web of fibers.

In another suitable method of bringing polymeric soft-surface fibers together, a non-woven web of staple fibers is formed, either via carding/through air bonding techniques, carding/needlepunching techniques, air laying techniques, or wet laying techniques.

After the fibers are brought together (by any method of bringing fibers together, including, for example, any of the methods described herein above), the web of fibers may suitably be, for example, processed by any of a wide variety of methods. In embodiments where a three dimensional bonded fiber structure is desired, an unbonded or lightly bonded fiber web may be heated and passed through a forming die to bond the fibers to each other at their points of contact, then cooled to provide a final three dimensional bonded fiber structure.

The arrangement, density, and material of the fibers and the fiber structure may be tailored to provide desired overall element porosity and fiber surface area. The materials and configuration of the fibers may also determine the degree to which the fibers attract or repel certain fluids. In particular embodiments, the three-dimensional structure contains fibers that provide a hydrophilic surface. For example, the three-dimensional structure may contain core-sheath fibers in which the sheath is hydrophilic. Melt-blown fibers may be made more or less hydrophilic by, for example, the use of hydrophilic or hydrophobic additives that are added to the melt prior to the blowing process or by other methods. Some fibers may be made more or less hydrophilic by, for example, the use of surface finishes, melt additives, or a combination thereof. Some suitable surface finishes contain, for example, surfactants, lubricating fluids, and mixtures thereof.

In some embodiments, the three-dimensional fiber structure is substantially isotropic; that is, its structural characteristics and resulting properties (e.g., density, porosity, surface area, surface energy, etc.) are substantially uniform throughout the structure.

Alternatively, however, the fiber structure may have characteristics that vary through the structure. In particular, the fiber structure may be comprised of two or more distinct components, each component having substantially uniform characteristics that differ from one or more of the other components. Certain fiber structures of this type are described in U.S. application Ser. No. 11/333,499, filed Jan. 17, 2006, the specification of which is incorporated herein by reference in its entirety. By varying material, or at times the fiber types and/or characteristics in each component, an anisotropic three-dimensional structure may be created. The components may differ in various characteristics, including but not limited to, material, density, porosity, surface area, surface energy, finish treatments, particulate loading, etc.

The powder particles that contain the encapsulation complex may be brought into contact with the fibers during or after the formation of the fibers and the fiber structure. The powder particles may be fixed to some or all of the fibers of the structure or otherwise contained within the fiber structure. The powder particles may be fixed to the fibers by any method. In some embodiments, the powder particles are fixed to the fibers through heat-bonding.

One method, for example, of bringing powder into a fiber structure is as follows. Powder may be distributed onto an unbonded or lightly bonded web of fibers, which is then drawn through a die heated with preferably hot air or, less preferably, steam to form a porous, bonded fiber rod, which is then cooled and cut to desired lengths. In some embodiments, powder that is trapped in this fiber rod is bonded to the exposed component of the fibers via the softening by heat and then re-solidification by cooling of that component on the fiber surface. In some embodiments, the powder may remain within the fiber structure even if all or part of the powder is not bonded to the fibers.

In some embodiments, it is contemplated that some or all of the powder particles, while bonded to the three-dimensional structure, are not fully enclosed by any material. That is, for some or all of the powder particles, some portion of the individual particle will be exposed to the atmosphere, even if some other portion of the same particle may be buried under or surrounded by some other solid material such as, for example, a portion of one of the components of a multicomponent fiber.

Regardless of the specific shape of the web of fibers, the powder may be distributed onto or into the web by any method. In some embodiments, the powder that contains encapsulation complex may be applied to the web in its form as manufactured, or it may be mixed with another powder (called herein a "diluent powder"). Suitable diluent powders are described herein above. One purpose for the use of one or more diluent powder, for example, is to allow the encapsulated complex to be distributed to the web in amounts that are uniform and/or accurate. For example, if it is desired to create a device that releases a certain amount of volatile compound, the designer would calculate the amount of encapsulated complex that should be bonded to the fibers of the device. If that amount of encapsulated complex is relatively small, it may prove difficult to apply the encapsulated complex in the form of the powder as it is manufactured, and it may be easier to control the accuracy and/or the uniformity if that powder is blended thoroughly with a diluent powder, because the method of gradually applying powder to the fibers may be easier to control if a larger amount of powder is being applied.

For example, if it is known that a certain device will be used for the purpose of releasing a concentration of 1 ppm of a volatile compound into a fixed volume of 1 liter, the designer can calculate how much encapsulation complex must be included in the device. If it is difficult to provide that desired amount accurately because of the small size of the amount, it may be easier to dilute the powder and then be able to accurately apply the desired amount of the diluted powder to the fibers.

For another example, if it is desired to produce a particular amount of volatile compound in a larger fixed volume (for example, 30 liters), or if a larger amount of encapsulation complex is desired in a device, it may be convenient to use less diluent powder, so that the amount of blended powder that must be applied to the fibers is not too large. Also, the amount of powder may be adjusted to yield the desired amount of volatile compound that is finally released.

Alternatively, instead of or in addition to altering the amount of applied powder or altering the amount of powdered diluent used, it may be convenient to use more or less volume of fiber structure while maintaining the relative amount of encapsulation complex or diluted encapsulation complex per unit volume. In this case, for example, a smaller fixed volume of container could be addressed by using less volume of bonded fiber structure. Conversely, a larger fixed volume of container could be accommodated by use of more volume of fiber structure. It will be understood that increasing the volume of fiber structure may be accomplished by increasing the size of a single fiber structure or providing multiple fiber structures.

In some embodiments, it may be desired to release the volatile compound into a container that is open to the atmosphere or partially open to the atmosphere. In such a case it may be desired to release volatile compound gradually, at a rate that is approximately constant and that is designed, given the conditions, to maintain a certain target concentration of volatile compound in the air near the device. It is contemplated that an appropriate device could be designed for such an embodiment, including selection of amount of diluent powder, if any, and of the amount of powder bonded to the fiber matrix of the device.

In various embodiments, it will be intended to expose the device to a liquid release compound, to expose the device to a gaseous release compound, or to expose the device to a mixture of liquid and gaseous release compound. It is contemplated that the type and amount of diluent powder, and the overall amount of powder, can be chosen to provide the desired amount of released volatile compound, given the nature of the intended release compound.

In some embodiments, the encapsulation complex is located in a portion of the three-dimensional fiber structure and is not located throughout the entire three-dimensional fiber structure.

For example, in a three dimensional fiber structure having multiple structural components with different characteristics (e.g., density, porosity, fiber surface energy, etc.), the encapsulation complex may be disposed within some structural components and not others. In a particular example, the fiber structure may have a plurality of layers with the outer fiber layers having different characteristics from at least one inner layer in which the encapsulation complex is enclosed.

In some embodiments (herein called "patch" embodiments) a three-dimensional fiber structure may be formed that is shaped like a rectilinear solid and is relatively small (i.e., less than 5 mm) in one dimension and relatively large (i.e., at least 2 cm) in each of the other two dimensions. In some patch embodiments, a layer of a composition may be applied to one or more of the relatively large flat faces (i.e., one or more of the faces that is perpendicular to the short dimension). Such a composition may be applied at ambient temperature (i.e., approximately 23° C.) or at elevated temperature. The layer of composition, after it is applied, may or may not be heated above the temperature at which it is applied. Such a composition may be applied as a solid mass, as a particulate solid, as a liquid (such as a molten liquid of a composition that is solid at 25° C., as a solution, or as a dispersion, or as some combination thereof). In some embodiments, a composition is applied to a portion of the flat face of the fiber structure and not to the entire flat face. The portion of the flat face to which the composition has been applied is referred to herein as a "stripe" of that composition.

In some patch embodiments, a layer of a composition that contains encapsulation complex is applied to a relatively large flat face of the fiber structure. For example, a liquid composition in which encapsulation complex is dissolved or dispersed may be applied to the face of the fiber structure, and the liquid portion of the composition may be dried or allowed to dry. In some of such embodiments, the encapsulation complex resides in a stripe on the flat face of the fiber structure.

In some embodiments, a flat face of the fiber structure, in addition to a layer of, a composition that contains encapsulation complex, also receives a layer of a composition containing one or more other materials. Some suitable "other materials" are, for example, the materials described above regarding materials that are suitable for blending with encapsulation complex in a powder Preferred other materials are water-absorbing materials. Preferred water-absorbing materials are deliquescent. A deliquescent material is capable, at 25° C. and at some range of relative humidity, of absorbing gaseous water from the atmosphere and forming a liquid solution of itself in water. Some suitable deliquescent materials are, for example, inorganic deliquescent salts, organic deliquescent compounds, and mixtures thereof. Suitable inorganic deliquescent salts include, for example, ammonium chloride, ammonium nitrate, ammonium sulfate, calcium chloride, magnesium sulfate, phosphoric acid, deliquescent salts of phosphoric acid, tetrasodium pyrophosphate, and mixtures thereof. Suitable organic deliquescent compounds include, for example, urea, sorbitol, deliquescent saccharides (including monosaccharides, disaccharides, oligosaccharides, and polysaccharides, such as, for example, maltodextrin), citric acid, deliquescent salts of citric acid (for example, sodium citrate), benzoic acid, boric acid, and mixtures thereof. Preferred deliquescent compounds are PEGs and blends of urea with a second deliquescent compound; more preferred are blends of urea with one or more of sorbitol, citric acid, and sodium citrate; more preferred is a mixture of urea and sorbitol.

A layer of other material (i.e., material other than encapsulation complex) may be placed over a layer of composition that contains encapsulation complex, under a layer of composition that contains encapsulation complex (by applying the layer of other material to the face of the fiber structure prior to applying the layer that contains encapsulation complex), or a combination thereof. Also suitable are embodiments in which a layer of other material is on a portion of a flat face of a fiber structure, and in which a layer of composition that contains encapsulation complex is also present on a portion of the same face of that fiber structure, and in which at least some of the layer of other material is in a place on the face of the fiber structure where there is no encapsulation complex.

Also contemplated are embodiments in which a first patch is formed, one or more layer of composition is applied to some or all of one flat face (the "coated" face) of the first patch, and then a second patch is applied to the first patch, so that one flat face of the second patch faces the coated face of the first patch, and the patches are adhered together by application of elevated temperature, pressure, an adhesive composition, or a combination thereof. Also contemplated are embodiments in which a structure is similarly made of three or more patches attached together, optionally with one or more composition applied to some or all of one or more of the flat faces of each patch.

Each patch of a multi-patch structure may be a bonded fiber component of an overall, integrally formed bonded fiber structure. As was previously described, each component of such a structure has its own set of material and fluid flow characteristics, which may be different from the characteristics of the other components of the structure. Application of the encapsulation complex (in the form of powder particles) as described above produces a multicomponent structure in which the encapsulation complex is disposed in a region of the interior of the structure. More particularly, the encapsulation complex is disposed in a volumetric region adjacent the interface between two bonded fiber components of the structure. The powder particles may be disposed between or adhered to fibers of either or both of the bonded fiber components.

When a layer of a composition of other material is present, it may serve any of a variety of purposes. While the present invention is not limited to any mechanism, it is contemplated that a layer of a composition that contains a deliquescent compound may operate by absorbing water, forming an aqueous solution of itself, and promoting the release of volatile compound from the molecular encapsulation agent through contact between the aqueous solution and the encapsulation complex. Also contemplated are embodiments in which an other material is used that absorbs water and sequesters the water; it is contemplated that such an other material could retard release of volatile compound by temporarily preventing water from contacting the encapsulation complex.

Some methods of using a device of the present invention involve bringing a release compound into contact with the three-dimensional fiber structure of the present invention. When considering such methods, it is useful to consider the nature of the interaction between the release compound and the fiber structure. For example, if the release compound is a liquid, the fiber structure may act, for example, as a wick and imbibe and/or transport the liquid. It is contemplated in such cases that the rate at which the fiber structure imbibes the liquid (the "wicking rate") is related to the tendency of the fiber structure to imbibe the liquid (the "capillary draw") of the device. While the present invention is not limited to any particular theory, it is contemplated that the capillary draw of the fiber structure will be related to the rate at which liquid release compound comes into contact with encapsulation complex and therefore will also be related to the time dependence of the release of volatile compound from the encapsulation complex.

The capillary draw of a fiber structure of the present invention is contemplated to depend on a variety of variables, including, for example, the shape of the cross section of the fibers, the area of the cross section of the fibers, the length of the fibers, and combinations thereof. For example, in some cases it is contemplated that fibers with smaller area of their cross section will have higher capillary draw.

Whether the release compound is a liquid or a gas, the tendency of the fiber structure to accept and/or draw the release compound into the voids is contemplated to be related to the interaction between the release compound and the surface of the fibers. In many cases, this interaction may be predicted from the surface energy of the fibers. For example, if the release compound is water, when the fibers have relatively high surface energy, it is contemplated that water (either liquid or gas or a combination thereof) will be more readily taken up by the fiber structure. The surface energy of the fibers may be controlled by any of the following variables or combinations thereof: surface coatings, additives, and choice of polymers(s).

For example, a surface coating may or may not be used. If a surface coating is used, the coating could be chosen or designed to give a surface having the desired surface energy. For another example, any one or more of the polymer(s) in the fiber could be used with or without one or more additive. If an additive is used, it could be chosen to impart the desired surface energy to the fiber. For another example, some polymers inherently have higher surface energy than others, so the polymer or polymer blend could be chosen to yield a fiber with the desired surface energy.

Another characteristic of a fiber structure of the present invention is the porosity (i.e., the void volume as compared to the overall volume of the fiber structure). It is contemplated that porosity may affect either the wicking properties of the fiber structure or the gas release rate (the rate at which the volatile compound escapes the fiber structure) or both. Therefore the fiber structure may be designed to have a porosity that gives the desired wicking properties and/or the desired gas release rate. Depending on the method used, porosity may also affect the ability to incorporate powder into the fiber structure during the manufacturing process.

It is contemplated that, in designing a fiber structure, various design variables could be chosen independently of each other in order to control all the desired properties of the final fiber structure. For example, it is contemplated that the cross-sectional area of the fibers could be chosen and the density with which fibers are brought together could also be chosen in order to control both the available surface area of the fiber structure and the porosity.

In some embodiments, most or all of the encapsulation complex will be bonded to the surface of a fiber or to the surface of a junction point between plural fibers. In such embodiments, it is contemplated that the surface area inside the fiber structure will be related to the amount of encapsulation complex that is available to be brought into contact with release compound and therefore available to release volatile compound.

Independently, it is further contemplated that, in general, higher porosity will allow for easier transport of gas through the fiber structure, which will lead to more facile transport of volatile compound out of the fiber structure after it is released from encapsulation complex.

It is contemplated that the rate of release of volatile compound can be varied depending on fiber structure characteristics. Therefore, it is further contemplated that multiple fiber structures could be used in a single apparatus to provide delivery at different rates. This could allow for a timed release approach. The multiple structures could, for example, be provided in a single integral bonded fiber structure, in separate structures bonded together to form a single device, or in multiple devices.

After the device is made, it is preferable to store the device in a way that prevents contact with any release compound. For example, if water is a release compound for a particular encapsulation complex, it is preferable to store a device that contains that encapsulation complex in a container that prevents contact with water until it is desired to release the volatile compound.

In some embodiments, the fiber structure of the present invention will be used as part of an apparatus or system for delivering a volatile compound to a target. It is contemplated that the apparatus for delivering a volatile compound to a target will be designed to hold the device of the present invention, to receive the target and/or to hold the target, and to allow release compound to come into contact with the device. For example, the apparatus could comprise both a container and one or more devices of the present invention. In some embodiments, one or more devices would be disposed within the container. The container could, for example, define a volume that was configured to receive the target and that was also configured to allow the volatile compound, when it is released, to contact the target. In order to allow the volatile compound to contact the target, the container could, for example, fully or partially enclose a volume.

For example, in some embodiments, one or more devices containing (or comprising) a fiber structure of the present invention could be affixed with a fastener to the inside of a container. Such devices could be affixed to the lid, to walls, to the bottom, or to a combination thereof. One suitable location for the device would be to affix it to the inside of the lid of a container underneath a label that is attached to the outside of that lid; thus the device would be in a place that was not visually prominent. Also, alternatively or additionally, one or more of such devices could be placed into such a container without being fastened. Also contemplated are embodiments in which a container is manufactured with one or more holder or enclosure that would hold one or more devices of the present invention. Also contemplated are embodiments in which container was manufactured with one or more devices of the present invention made as part of the container.

Containers used in volatile compound delivery apparatus of the invention may be configured for packaging of target materials for transport, storage, display or sale. Examples of container materials include but are not limited to plastic, paperboard, metal and composite materials of multiple laminates and structures.

In some embodiments, one or more volatile compound delivery devices of the present invention could be disposed on the outside of a container configured for holding a target material. In such embodiments, a portion of a wall of the container may be configured to be porous. This may be accomplished by providing holes extending through the wall from the interior of the container to the exterior of the container. The one or more devices are affixed to the exterior of the container over the porous area of the container wall, which allows the atmosphere inside the package to interact with the one or more compound delivery devices.

In use, the one or more compound delivery devices would be exposed to the atmosphere of the container and any release compound included therein. Interaction between a sufficient amount of the release compound and the volatile compound delivery device(s) results in release of the volatile compound back into the interior of the container for interaction with the target material.

Additional layers or materials such as plastic film or other moisture impervious membrane may be placed over the outward-facing surface of the fiber structures of the one or more delivery devices to prevent exposure of the volatile compound to the atmosphere external to the container. These additional layers or materials may, for example, be incorporated into a label or other secondary packaging layer.

In some embodiments, a removable film or material layer may be applied to the interior of the porous portion of the container wall. This isolates the volatile compound delivery device(s) on the exterior of the container from the interior atmosphere of the container until the removable film or material layer is removed. This would allow for pre-assembly and storage of containers without concern of exposure or contamination of the delivery devices. When a container is to be used, the target material is placed in the container interior, the removable film or material layer is removed, and the container is sealed.

Devices of the present invention could, for example, be stored, prior to placement into such a container, in an environment free of release compounds. Also, such devices could be placed in such a container (by any of the methods described herein above or by any combination thereof), and the container could be stored in an environment free of release compounds. Such a device or container could be removed from the environment free of release compounds when it is desired to release the volatile compound.

In certain exemplary embodiments (herein called "produce" embodiments) the volatile compound incorporated into the volatile compound delivery device is a cyclopropene compound and the target comprises plants or plant parts. In some produce embodiments, it is contemplated that one or more delivery device of the present invention could be placed in a container with plants or plant parts and that the plants or plant parts would release gaseous water into the atmosphere in the container, and that gaseous water could act as release agent to release the cyclopropene compound into the atmosphere of the container, where it would come into contact with the plants or plant parts.

In some produce embodiments, the plants or plant parts could be, for example, whole plants (such as, for example, flowering plants), cut flowers, whole vegetables, cut-up vegetables, whole fruits, cut-up fruits, or a combination thereof.

In some produce embodiments, the container may be sealed, or the container may allow air to exchange with the surrounding atmosphere.

One suitable type of container for produce embodiments is a rigid plastic container called a clamshell container.

In some produce embodiments, cut flowers are placed into a box. One or more device of the present invention could be removed from an atmosphere free of release agents (such as, for example, the inside of a sealed foil pouch) and placed into the box containing the flowers. Ambient humidity could act as a release agent to release cyclopropene compound into the atmosphere of the box, where it could contact the cut flowers.

It is contemplated that embodiments of the present invention include any arrangement of one or more device of the present invention in circumstances in which release compound contacts a device and releases the volatile compound in a way that allows volatile compound to come into contact with one or more target.

It is contemplated that the methods of the present invention may be practiced at any temperature. In some embodiments, room temperature (20° C.) is used. In some embodiments, it is desirable to practice the methods of the present invention at other temperatures. For example, in some produce embodiments, it may be desirable to release cyclopropene compound in proximity to plants or plant parts while the plants or plant parts are stored at a temperature below room temperature, and in such embodiments the temperature may be chosen to prolong the storage life of the plants or plant parts.

In some embodiments, a device containing the three-dimensional structure is brought into contact with a release compound, and the volatile compound releases from the encapsulation complex and enters the atmosphere. For example, when the volatile compound is a cyclopropene compound and the molecular encapsulation agent is a cyclodextrin, water (in either liquid or gaseous state) is one effective release compound. When such a device of the present invention is brought into contact with water, the cyclopropene will be released to the atmosphere. The water may be in the form of pure water or in the form of an aqueous composition (i.e., a composition that contains 25% or more water by weight, based on the weight of the aqueous composition).

One purpose for releasing cyclopropene compound into the atmosphere is the treatment of plants or plant parts. Cyclopropene compounds are known to inhibit the ethylene response of plants or plant parts. Some beneficial effects of contact between plants or plant parts and cyclopropene compounds include, for example, improvements in crop yield and/or in stress resistance (when whole plants are contacted) and prolonging the storage time at which plant parts maintain good quality (when plant parts are contacted).

When it is desired to contact plants or plant parts with one or more cyclopropene compounds that are released from a device of the present invention, the plants or plant parts should be in proximity to the device when the cyclopropene is released. By "proximity" it is meant that a significant amount of the cyclopropene compound will contact the plant prior to escaping to the atmosphere. Proximity may be achieved by placing both the device and the plants or plant parts in the same enclosed container; or by placing both the device and the plants or plant parts in the same container that has a relatively small opening; or by placing the plants or plant parts sufficiently close to the device.

Contact between the device and an aqueous composition in proximity to plants or plant parts may be performed by any method. For example, some suitable methods include the following: placing the device and the plants or plant parts in a container with an atmosphere with sufficient humidity to release the volatile cyclopropene compound; bringing the device into contact with a liquid aqueous composition and then placing the wet device and the plants or plant parts in the same container; and placing and keeping the device in a liquid aqueous composition in a small container, which is present in a larger container that also contains the plants or plant parts.

Any plants or plant parts are suitable for use in the present invention, including, for example, whole plants or harvested plant parts from categories that include, for example, cereals, roots and tuber plants, sugar crops, pulses (including, for example, beans, chickpea, garbanzo, black-eyed pea, pigeon pea, lentil, and other pulses), nuts, stimulant crops (including, for example, coffee, cocoa bean, tea, and mate) and oil-bearing crops (including, for example, peanuts and soybeans).

Further examples of suitable plants or plant parts include, for example, vegetables, including, for example, cabbages, artichokes, asparagus, lettuce, spinach, cassava leaves, tomatoes, cauliflower, pumpkins, cucumbers and gherkins, eggplants, chilies and peppers, green onions, dry onions, garlic, leek, other alliaceous vegetables, green beans, green peas, green broad beans, string beans, carrots, okra, green corn, mushrooms, watermelons, cantaloupe melons, bamboo shoots, beets, chards, capers, cardoons, celery, chervil, cress, fennel, horseradish, marjoram, oyster plant, parsley, parsnips, radish, rhubarb, rutabaga, savory, scorzonera, sorrel, watercress, and other vegetables.

Further examples of suitable plants or plant parts include, for example, fruits, including, for example, bananas and plantains; citrus fruits; pome fruits; stone fruits; berries; grapes; tropical fruits; miscellaneous fruits; and other fruits.

DESCRIPTIONS OF SELECTED EMBODIMENTS

Among the embodiments of the present invention, some examples are the following:

In a first embodiment, there is a device comprising
(a) a three-dimensional structure comprising a plurality of fibers, and
(b) powder particles contained in or affixed to said structure, wherein said powder particles comprise one or more volatile compound in an encapsulation complex with a molecular encapsulation agent.

In a second embodiment, there is a device of the first embodiment, wherein said fibers comprise one of the set consisting of a plurality of multicomponent polymeric fibers, a plurality of monocomponent fibers, and a combination of multicomponent fibers and monocomponent fibers.

In a third embodiment, there is a device of the first embodiment, wherein said fibers are bonded to one another at spaced-apart contact points to form a self-sustaining fluid-transmissive body, the fibers collectively defining tortuous fluid flow paths through the fluid transmissive body.

In a fourth embodiment, there is a device of the second embodiment, wherein the powder particles are distributed throughout the three dimensional structure.

In a fifth embodiment, there is a device of the first embodiment, wherein the three dimensional structure comprises a plurality of integrally formed structural components, each of which is a three-dimensional, fluid transmissive structure comprising a plurality of the fibers bonded to one another at spaced apart contact points, the bonded fibers collectively defining tortuous fluid flow paths, and wherein each fluid transmissive component has substantially uniform fluid flow characteristics.

In a sixth embodiment, there is a device of the fifth embodiment wherein the powder particles are distributed throughout at least one of the plurality of integrally formed structural components.

In a seventh embodiment, there is a device of the fifth embodiment wherein the powder particles are disposed in a volumetric region adjacent an interface between two of the plurality of integrally formed structural components.

In an eighth embodiment, there is a device of the first embodiment wherein said encapsulating compound is selected and configured to release the volatile compound when said encapsulation complex comes into contact with a predetermined release compound.

In a ninth embodiment, there is a device of the eighth embodiment wherein the predetermined release compound is liquid water or gaseous water, said volatile compound comprises one or more cyclopropene compound, and said molecular encapsulating agent comprises one or more cyclodextrin.

In a tenth embodiment, there is a device of the eighth embodiment wherein the three dimensional structure is configured and at least a portion of the fibers are selected so that the three dimensional structure wicks the predetermined release compound when the predetermined release compound contacts a surface of the three dimensional structure.

In an eleventh embodiment, there is a device of the first embodiment wherein at least a portion of a surface defined by the fibers is hydrophilic.

In a twelfth embodiment, there is a method of releasing a volatile compound, the method comprising providing a release device comprising
(a) a three-dimensional structure comprising a plurality of fibers, and
(b) powder particles contained in or affixed to said structure, wherein said powder particles comprise one or more volatile compound in an encapsulation complex with a molecular encapsulation agent.

The method further comprises bringing the predetermined release complex into contact with the molecular encapsulation complex so that the molecular encapsulation complex releases the volatile compound.

In a thirteenth embodiment, there is a method of the twelfth embodiment wherein the three dimensional structure is configured and at least a portion of the fibers are selected so that the three dimensional structure wicks the predetermined release compound when the predetermined release compound contacts a surface of the three dimensional structure, and wherein the action of bringing the predetermined release complex into contact with the molecular encapsulation complex comprises causing or allowing the predetermined release compound to contact a surface of the three dimensional structure.

In a fourteenth embodiment, there is a method of the twelfth embodiment wherein the predetermined release compound comprises water.

In a fifteenth embodiment, there is a method of the fourteenth embodiment further comprising placing the release device in proximity to plants or plant parts.

In a sixteenth embodiment, there is a method of the fourteenth embodiment wherein the action of bringing the predetermined release complex into contact with the molecular encapsulation complex comprises placing plants or plant parts in an interior space of a container, and positioning the release device so that it is in fluid communication with an atmosphere of the interior space.

In a seventeenth embodiment, there is a method of the sixteenth embodiment wherein the action of positioning the release device includes placing the release device in the interior space of the container.

In an eighteenth embodiment, there is a method of the sixteenth embodiment wherein at least a portion of a wall of the container is porous to allow fluid communication therethrough and the action of positioning the release device includes attaching the release device to an outside surface of the at least a portion of a wall.

In a nineteenth embodiment, there is a method of the twelfth embodiment wherein said volatile compound comprises one or more cyclopropene compound, and wherein said molecular encapsulating agent comprises one or more cyclodextrin.

In a twentieth embodiment, there is an apparatus for delivering a volatile compound to a target, the apparatus comprising a container defining an interior space configured for receiving the target and at least one release device comprising
(a) a three-dimensional structure comprising a plurality of fibers, and
(b) powder particles contained in or affixed to said structure, wherein said powder particles comprise one or more volatile compound in an encapsulation complex with a molecular encapsulation agent selected and configured to release the volatile compound when said encapsulation complex comes into contact with a predetermined release compound, and
the at least one release device being disposed so that it is in fluid communication with an atmosphere of the interior space.

In a twenty-first embodiment, there is an apparatus of the twentieth embodiment wherein the release device is disposed in the interior space of the container.

In a twenty-second embodiment, there is an apparatus of the twentieth embodiment wherein at least a portion of a wall of the container is porous to allow fluid communication therethrough and the release device is attached to an outside surface of the at least a portion of a wall.

In a twenty-third embodiment, there is an apparatus of the twentieth embodiment wherein said volatile compound comprises one or more cyclopropene compound, and wherein said molecular encapsulating agent comprises one or more cyclodextrin.

EXAMPLES

In the following examples, devices were formed using bicomponent polyethylene (sheath)/polypropylene (core) fibers and powder. The fibers were formed into a three-dimensional structure, the powder was applied, and the structure was heat treated.

The unmodified powder (called "std" powder herein) contained encapsulation complex of 1-methylcyclopropene (1-MCP) and alpha-cyclodextrin and a small amount of alpha-cyclodextrin. The amount of 1-MCP in the std powder was 4.7% by weight, based on the weight of the powder.

Heating with steam had more tendency than hot-air heating to reduce the amount of 1-MCP that could be eventually released. The examples below used hot air heating.

Three-dimensional structures were formed into continuous cylindrical rods and then cut to dimension.

The following chemical test procedures were used. The chemical test procedures were performed at room temperature (approximately 20° C.).

Chemical Test Procedure—Total Release

The device to be tested was placed in the bottom of a glass bottle equipped with a septum seal. Deionized water was injected, fully wetting the device. The bottle was agitated for one hour to affect release from the device and to equilibrate the dissolved 1-methylcyclopropene with the air in the bottle. The concentration of 1-methylcyclopropene was analyzed and quantitated by gas chromatography using external standards of known concentration.

Chemical Test Procedure—Release via humidity

The device to be tested was adhered (via tape or a glue-dot) to the inside of the neck of a glass bottle equipped with a septum seal. Deionized water was injected, taking care not to wet the device. The bottle was stored at the test temperature. At appropriate time intervals, the concentration of 1-methylcyclopropene was analyzed and quantitated by gas chromatography using external standards of known concentration.

Example 1

Release via Humidity

Each device was 5 mm diameter and 6 mm length. In some devices, PEG-1000 (poly ethylene glycol, molecular weight 1000) was added to the powder prior to distribution of the powder to the fiber structure, the amount of PEG-1000 was 10% by weight based on the weight of the powder.

TABLE 1

| PEG-1000 | Powder | Humidity | Elapsed Hours | % Release |
| --- | --- | --- | --- | --- |
| 10% | 10 mg | 100% | 7.5 | 100% |
| 10% | 10 mg | 80% | 23 | 45% |
| 0% | 20 mg | 100% | 7.5 | 85% |
| 0% | 20 mg | 80% | 23 | 20% |

Higher release percentages of 1-MCP were obtained at higher humidity levels and when PEG 1000 was employed.

Example 2

Total Release of 1-MCP

Devices were made as described above. In some cases, the "std" powder (defined herein above) was used (median particle size 20 micrometers), and in other cases it was airmilled prior to use ("AM," resulting median particle size of 5 micrometers). In some samples, the std powder was diluted with a diluent powder at a weight ratio of 10 parts of the diluent powder to 1 part std powder. Diluent powders were either sodium bicarbonate ("BS") or molecular sieves of 3-angstrom size ("MS3"). In some samples, PEG-1000 was added to the powder at 10% PEG-1000 based on the weight of the powder.

The total release (in micrograms of 1-MCP per device) was measured as described herein above for some of the devices. Seven replicates of each device were tested, and the average is reported.

TABLE 2A

| Sample | Powder | Diluent | PEG 1000 | 1-MCP released (microgram) |
|--------|--------|---------|----------|----------------------------|
| 2-A | Std | none | No | |
| 2-B | Std | BS | No | |
| 2-C | Std | BS | Yes | |
| 2-D | Std | BS | No | 1.36 |
| 2-E | Std | BS | Yes | 1.42 |
| 2-F | AM | BS | No | |
| 2-G | AM | BS | No | 0.52 |
| 2-H | Std | MS3 | No | |
| 2-I | Std | MS3 | No | 0.79 |
| 2-J | AM | MS3 | No | |
| 2-K | AM | MS3 | No | 0.65 |

Example 3

Total Recovery of 1-MCP

Devices were made and tested as in Example 2. Powders were Std, a premixed blend ("PB3-3") of Std (2 parts by weight) plus PEG (1 part by weight) plus MS4 (8 parts by weight), and a premixed blend ("PB3-4") of Std (2 parts by weight) plus PEG (1 part by weight) plus MS3 (8 parts by weight). Diluents were either BS or polyvinyl alcohol (PVA) or 4-angstrom Molecular sieves (MS4).

The devices were studied for total release of 1-MCP. The results (the average of 7 replicate samples) are shown in Table 3.

TABLE 3

| Sample | Powder | Diluent | ratio | 1-MCP released (microgram) |
|--------|--------|---------|-------|----------------------------|
| 3-1-B | Std | none | | 15.5 |
| 3-1-C | Std | BS | 1:1 | 25.6 |
| 3-1-D | AM | none | | 1.8 |
| 3-1-E | Std | PVA | 1:1 | 45.2 |
| 3-1-F | Std | none | | 26.7 |
| 3-1-G | Std | BS | 1:10 | 5.9 |
| 3-2-B | PB3-3 | none | | 2.3 |
| 3-2-C | PB3-4 | none | | 3.3 |

Example 4

Test on Pears

Bartlett Pears were placed unwrapped loose in a box (0.5 m by 0.23 m by 0.3 m). The device used was Example 2-A. Pears were placed into the box along with zero, 1, or 2 devices, and the lid was closed. The box was placed in a plastic bag with microperforations, open at one end. Temperature was room temperature, approximately 20° C. The pears were cold (1° C. to 5° C.) when placed in the box; condensation may have occurred in the box). The arrangement was held constant for 9 days, whereupon the devices were removed. The pears were evaluated at 9 days, at 15 days, and at 22 days for hue angle (change from green to yellow, using a Minolta colorimeter) and for flesh firmness with a Fruit Texture Analyzer (from Guss Manufacturing Ltd, in South Africa) fitted with a tip of 8 mm diameter. From each box, 25 pears were tested.

Firmness results are shown in kg, with the standard deviation shown in parentheses).

TABLE 4

| | firmness in kg (STDev) | | | Hue Angle (STDev) | | |
|---------|-------|--------|--------|--------|--------|--------|
| Devices | day 9 | day 15 | day 22 | day 9 | day 15 | day 22 |
| 0 | 0.7 (0.2) | 0.3 (0.1) | | 94.0 (1.5) | 90.0 (1.3) | 87.1 (2.3) |
| 1 | 6.2 (1.7) | 2.2 (1.7) | 0.9 (0.5) | 108.1 (4.5) | 95.9 (3.3) | 89.2 (2.4) |
| 2 | 7.0 (0.7) | 4.4 (1.7) | 2.0 (1.70) | 109.8 (2.2) | 101.5 (3.7) | 91.1 (2.4) |

Example 5

Second Test on Pears

Pears were tested as in Example 4. In one sample, one device was used, but it was placed in a small beaker and then set inside the box, to isolate the device from any condensation. Also, one set of pears ("Comp" i.e., comparative) was treated with the SmartFresh™ system (AgroFresh, Inc.), which involves contact with gaseous 1-MCP at 600 parts per billion (by volume based on volume of atmosphere) in an enclosed room or container for 24 hours; then the pears were placed in a box and a bag, just like the other samples but without any device. All samples were evaluated at 7 days and 14 days.

TABLE 5

| Devices | firmness in kg (STDev) | | Hue Angle (STDev) | |
|---|---|---|---|---|
| | day 7 | day 14 | day 7 | day 14 |
| 0 | 1.2 (0.4) | 0.4 (0.1) | 96.9 (2.2) | 89.6 (1.8) |
| 1 | 3.8 (3.0) | 1.8 (2.0) | 102.5 (6.0) | 93.1 (4.0) |
| 1 (beaker) | 1.9 (1.3) | 0.6 (0.3) | 99.8 (4.1) | 91.4 (1.6) |
| Comp | 7.6 (0.6) | 4.0 (1.3) | 110.1 (1.0) | 99.9 (3.3) |

Example 6

Third Test on Pears

Pears were tested as in Example 4, except that the pears were wrapped in tissue paper and except that the plastic bags were sealed for 7 days after the pears were placed into the boxes. In one box, one device was placed in the box along with 1 ml of water.

TABLE 6

| Devices | firmness in kg (STDev) | | Hue Angle (STDev) | |
|---|---|---|---|---|
| | day 7 | day 14 | day 7 | day 14 |
| 0 | 1.0 (0.2) | 0.5 (0.2) | 94.2 (1.6) | 91.1. (0.8) |
| 1 | 3.2 (1.7) | 1.0 (0.5) | 103.5 (2.3) | 93.1 (1.0) |
| 2 | 5.6 (1.1) | 2.5 (1.5) | 106.1 (1.8) | 95.1 (3.0) |
| 1 (plus water) | 2.2 (1.2) | 0.7 (0.3) | 104.8 (2.8) | 92.0 (1.0) |

Example 7

Test on Carnations

Carnations were treated using devices like Example 2-A or using sachets of EthylBloc™ technology (from AgroFresh, Inc.). EthylBloc™ samples are comparative. Cut carnations were placed in boxes (170 liters) and the boxes and vents were closed. The four treatments were these: no devices; 3 dry devices per box; 3 devices per box, each placed in a beaker with 1 ml of water ("wet devices"); and EthylBloc™ sachets according to manufacturer's instructions. The boxes with devices or sachets were put into sealed chambers (900 liters) to prevent cross contamination. All boxes were stored at 3° C.

After 1 day of storage at 3° C., the wet devices and the EthylBloc™ sachets were removed from the boxes. A sample of flowers was removed from each box (for ethylene challenge testing) and the boxes were returned to storage at 3° C. for 7 days. The boxes with no devices or sachets and the boxes with dry devices were kept in the sealed chambers to prevent cross contamination.

The flowers that were removed after 1 day of storage at 3° C. were placed in vases in commercial vase life solution, and the vases were placed in a sealed chamber at 20° C. for 36 hours with atmosphere that contained 2 ppm (by volume, based on the volume of the atmosphere) of ethylene. These flowers were evaluated for vase life (the average number of days at 20° C. taken for each flower to become unacceptable). Each treatment had 4 replicates of 25 flowers each. Results were as follows:

TABLE 7A

| | Treatment: | | | |
|---|---|---|---|---|
| | none | dry devices | wet devices | EthylBloc ™ |
| Vase Life | 9.6 days | 11.4 days | 12.8 days | 12.0 days |

Statistical analysis showed that "none" was in one category and the other three treatments were in a second category.

Another group of carnations was stored at 3° C. for 7 days (to simulate typical shipping periods of flowers), held at 20° C. for two days, and then placed in a pear ripening room at 20° C. for 24 hours for ethylene challenging. This group was also evaluated for vase life using the same procedure as described above. Each treatment had 10 replicates of 25 flowers each. Results were as follows:

TABLE 7B

| | Treatment: | | | |
|---|---|---|---|---|
| | none | dry devices | wet devices | EthylBloc ™ |
| Vase Life | 9.2 days | 12.5 days | 13.1 days | 12.7 days |

Statistical analysis showed that "none" was in one result category and the other three treatments were in a second category and that wet devices performed better than dry devices.

Example 8

Storage of Devices

Immediately after forming and cutting some devices, they were placed into metalized plastic pouches containing silica desiccant. The powder used was Std powder diluted with BS, with proportion of Std to BS of either 1:10 or 1:15.

Based on the operation rates of the equipment used to make the devices and distribute the powder onto the devices, and based on the composition of the powder, the amount of 1-MCP on each device was calculated. The devices were later removed from the pouches and exposed to water, and the total 1-MCP released per device was measured. The results were as follows:

TABLE 8

| | dilution: | | | | | |
|---|---|---|---|---|---|---|
| | 1:10 | 1:10 | 1:10 | 1:15 | 1:15 | 1:15 |
| calculated 1-MCP (micrograms) | 11.98 | 7.91 | 12.28 | 4.85 | 7.03 | 8.60 |
| measured 1-MCP (micrograms) | 9.18 | 9.78 | 13.2 | 6.13 | 3.9 | 7.79 |

The amount of 1-MCP released is very close to the amount that is calculated to be present. It is considered that differences between the calculated and measured amount of 1-MCP is largely due to uncertainties that affect the calculation of the calculated amount.

Example 9

Use of Urea/Sorbitol

Devices were made as in Examples 1-8, using std. powder, and the three-dimensional fiber structures were in the form of patches. A molten mixture of urea and sorbitol was made at 100 to 130° C. and applied to patches. The weight ratio of molten mixture to std powder was 3:1. Alternatively, PEG was melted and applied to patches also at ratio of 3:1.

Patches were tested for release via humidity as described above. Tests were performed at 4° C. and 80% RH. Results were as follows:
Solution 1=Urea:Sorbitol at 80:20 by weight
Solution 2=Urea:Sorbitol at 60:40 by weight
Percent 1-MCP Released

| time (hr) | Solution 1 | Solution 2 | PEG |
|---|---|---|---|
| 1 | 9.68 | 13.48 | 25.67 |
| 2 | 14.09 | 17.58 | 30.83 |
| 3 | 17.39 | 21.04 | |
| 24 | 47.44 | 49.38 | 53.63 |
| 48 | 64.14 | 61.45 | 58.86 |
| 72 | 69.85 | 67.80 | 62.46 |
| 168 | 79.32 | 77.63 | 68.47 |
| 216 | 82.12 | 80.00 | 70.6 |

Additionally, Aging Stability was by storing the patch with the stripe of water-absorbing material at 54° C. for a fixed time and then testing the total 1-MCP release as described above. Results were as follows:

% Release of 1-MCP

| Sample | 2 days | 14 days |
|---|---|---|
| solution 1 | 96 | 88 |
| solution 2 | 97 | 80 |

Example 10

Placement of PEG

Devices were made as in Examples 1-8, using no powder, and the three-dimensional fiber structures were in the form of patches. Each patch received two stripes: one contained std powder and the other contained PEG (molecular weight 1,000). The two stripes were applied either one on top of the other or else side by side. Samples were made as follows:

| Sample | first stripe | weight ratio PEG:std powder | Location |
|---|---|---|---|
| 10-B | PEG | 2:1 | side by side |
| 10-E | std powder | 2:1 | side by side |
| 10-F | std powder | 2:1 | PEG on top |
| 10-G | std powder | 1:1 | PEG on top |

Results of release via humidity at 80% RH and 4° C. were as follows:
Percent 1-MCP Release

| Sample | 24 hrs | 48 hrs | 120 hrs | 144 hrs | 168 hrs |
|---|---|---|---|---|---|
| 10-B | 41.33 | 44.36 | 46.35 | | 47.34 |
| 10-E | 49.91 | 50.84 | 51.71 | | 54.08 |
| 10-F | 73.94 | 76.33 | 77.11 | | 77.71 |
| 10-G | 68.93 | 70.94 | 72.52 | 73.27 | 73.17 |

Example 11

Types of PEG

Samples were made like sample 10-G above except that the weight ratio of PEG to std powder was 3:1. Molecular weight (MW) of PEG was either 1,000 or 8,000. Release via humidity was tested at 4° C. and 80% RH, with the following results:
Percent 1-MCP Released

| PEG MW | 1 day | 2 days | 3 days | 6 days | 7 days |
|---|---|---|---|---|---|
| 1,000 | 59.05 | 67.83 | | | 82 |
| 8,000 | 33.92 | 45.65 | 49.93 | 51.62 | |

These samples were also tested for aging stability at 54° C. by measuring the total 1-MCP released after storage. Results were as follows:
Percent 1-MCP Released

| PEG MW | 2 day | 14 days |
|---|---|---|
| 1,000 | 62.69 | 60.63 |
| 8,000 | 86.15 | 92.92 |

Example 12

PEG vs. Sugar

Four types of patches were made as follows, with weight ratio of water-absorbent material (PEG or sugar) of 3:1. Sugar was white sugar suitable for human consumption. The white sugar powder was mixed along with Std. powder, sodium bicarbonate, and molecular sieve. Samples were as follows:
Example 12-A: Patches were made using powder that contained Std powder and PEG as in Example 1, with weight ratio of PEG to Std powder of 3:1, tested at 80% RH and 4° C.
Example 12-B: Patches as in 12-A, with sugar also used, tested at 100% RH and 22° C. In this example, we replaced PEG with sugar at a ratio of 3:1::sugar:Std. powder.
Example 12-C: Patches as in 12-B, tested at 80% RH and 4° C.
Example 12-D: Patches were made as in Example 1, with Std powder and no PEG. Sugar was not used, tested at 80% RH and 4° C.
Results for 1-MCP release via humidity were as follows:
Percent release of 1-MCP:

| Time (hrs) | 12-A | 12-B | 12-C | 12-D |
|---|---|---|---|---|
| 0.5 | 15.29 | | | 9.55 |
| 1 | 25.67 | 48.76 | 15.45 | 17.35 |
| 2 | 30.83 | | | 19.39 |
| 4 | 37.68 | 84.25 | 22.82 | 22.25 |
| 8 | 44.52 | 97.07 | 26.72 | |
| 16 | 50.68 | | | |
| 24 | 53.63 | 102.18 | 43.30 | 35.55 |
| 48 | 58.86 | 102.72 | 47.48 | 44.63 |
| 72 | 62.46 | 102.84 | 49.01 | 47.73 |
| 96 | 64.98 | | 50.69 | |
| 168 | 68.47 | | 53.02 | 53.72 |
| 192 | 69.66 | | 53.55 | 54.94 |
| 216 | 70.60 | | 54.28 | |
| 240 | 71.47 | | 54.95 | |
| 264 | 72.98 | | 55.27 | |

These samples were also tested for aging stability at 54° C. by measuring the total 1-MCP released after storage. Results were as follows:

Percent 1-MCP Released

| Sample | 2 day | 14 days |
|---|---|---|
| 12-A | 82.02 | 69.68 |
| 12-B | 93.90 | 90.06 |

We claim:

1. A device comprising
   (a) a three-dimensional structure comprising a plurality of fibers, and
   (b) powder particles contained in or affixed to said structure, wherein said powder particles comprise one or more volatile compound in an encapsulation complex with a molecular encapsulation agent wherein molar ratio of molecular encapsulating agent to volatile compounds is 0.95:1 to 1.5:1.

2. The device of claim 1, wherein said fibers comprise a plurality of multicomponent polymeric fibers, a plurality of monocomponent fibers, or a combination of multicomponent fibers and monocomponent fibers.

3. The device of claim 1, wherein said fibers are bonded to one another at spaced-apart contact points to form a self-sustaining fluid-transmissive body, the fibers collectively defining tortuous fluid flow paths through the fluid transmissive body.

4. The device of claim 1 wherein the powder particles are distributed throughout the three dimensional structure.

5. The device of claim 1, wherein the three dimensional structure comprises a plurality of integrally formed structural components, each of which is a three-dimensional, fluid transmissive structure comprising a plurality of the fibers bonded to one another at spaced apart contact points, the bonded fibers collectively defining tortuous fluid flow paths, and wherein each fluid transmissive component has uniform fluid flow characteristics.

6. The device of claim 5 wherein the powder particles are distributed throughout at least one of the plurality of integrally formed structural components.

7. The device of claim 5 wherein the powder particles are disposed in a volumetric region adjacent an interface between two of the plurality of integrally formed structural components.

8. The device of claim 1, wherein said molecular encapsulation agent is selected and configured to release the volatile compound when said encapsulation complex comes into contact with a predetermined release compound.

9. The device of claim 8 wherein the predetermined release compound is liquid water or gaseous water, said volatile compound comprises one or more cyclopropene compound, and said molecular encapsulating agent comprises one or more cyclodextrin.

10. The device of claim 8 wherein the three dimensional structure is configured and at least a portion of the fibers are selected so that the three dimensional structure wicks the predetermined release compound when the predetermined release compound contacts a surface of the three dimensional structure.

11. The device of claim 1 wherein at least a portion of a surface defined by the fibers is hydrophilic.

* * * * *